United States Patent [19]

Otabe et al.

[11] Patent Number: 5,765,119
[45] Date of Patent: Jun. 9, 1998

[54] METHOD AND DEVICE FOR ESTIMATING HYDROPLANING-OCCURING VEHICLE SPEED AND METHOD AND DEVICE FOR DETECTING POSSIBILITY OF OCCURENCE OF HYDROPLANING

[75] Inventors: Makoto Otabe; Ichiro Harada; Yuuichi Okada; Atsushi Itagaki; Yorihisa Yamamoto, all of Wako, Japan

[73] Assignee: Honda Giken Kogyo Kabushiki Kaisha, Tokyo, Japan

[21] Appl. No.: 579,274

[22] Filed: Dec. 27, 1995

[30] Foreign Application Priority Data

Dec. 29, 1994 [JP] Japan .................................. 6-339795

[51] Int. Cl.$^6$ .................................................. G01N 19/02
[52] U.S. Cl. .................. 701/82; 701/59; 701/74; 701/80; 701/90
[58] Field of Search .................. 364/426.041, 426.029, 364/426.027, 426.025, 426.018, 426.015, 424.085, 424.088, 426.036, 426.037; 434/305, 373, 376

[56] References Cited

U.S. PATENT DOCUMENTS

| | | | |
|---|---|---|---|
| 4,897,597 | 1/1990 | Whitener | 324/693 |
| 5,032,821 | 7/1991 | Domanico et al. | 340/440 |
| 5,050,940 | 9/1991 | Bedford et al. | 303/100 |
| 5,273,315 | 12/1993 | Debus | 280/762 |
| 5,350,035 | 9/1994 | Bodier et al. | 180/271 |
| 5,424,714 | 6/1995 | Kin et al. | 340/438 |
| 5,481,455 | 1/1996 | Iwata et al. | 364/424.01 |
| 5,521,594 | 5/1996 | Fukushima | 340/901 |
| 5,532,678 | 7/1996 | Kin et al. | 340/438 |
| 5,586,028 | 12/1996 | Sekine et al. | 364/423.098 |

FOREIGN PATENT DOCUMENTS

| | | |
|---|---|---|
| 6-50878 | 2/1994 | Japan . |
| 7-156782 | 6/1995 | Japan . |

*Primary Examiner*—Jacques H. Louis-Jacques
*Assistant Examiner*—Russell W. Frejd
*Attorney, Agent, or Firm*—Armstrong, Westerman, Hattori, McLeland & Naughton

[57] ABSTRACT

The hydroplaning-occurring speed of a vehicle is estimated by detecting an amount of water on a wet road surface on which the vehicle is traveling, and estimating a speed of the vehicle at and above which a hydroplaning phenomenon can occur, based on the detected amount of water. The possibility of occurrence of a hydroplaning phenomenon of a vehicle is detected by detecting an amount of water on a wet road surface on which the vehicle is traveling, detecting the speed of the vehicle, and determining whether there is a possibility that a hydroplaning phenomenon can occur, based on the detected amount of water and the detected speed of the vehicle.

7 Claims, 7 Drawing Sheets

FIG.7

| VEHICLE SPEED / AMOUNT OF WATER | ~10Km/h | ~20Km/h | ~30Km/h | ..... | ~80Km/h | ~90Km/h | ..... |
|---|---|---|---|---|---|---|---|
| 0 | 0 | 0 | 0 | ..... | 0 | 0 | ..... |
| 1 | 0 | 0 | 0 | ..... | 0 | 0 | ..... |
| 2 | 0 | 0 | 0 | ..... | 0 | 1 | ..... |
| 3 | 0 | 0 | 0 | ..... | 1 | 1 | ..... |
| 4 | 0 | 0 | 0 | ..... | 1 | 2 | ..... |
| 5 | 0 | 0 | 0 | ..... | 2 | 2 | ..... |

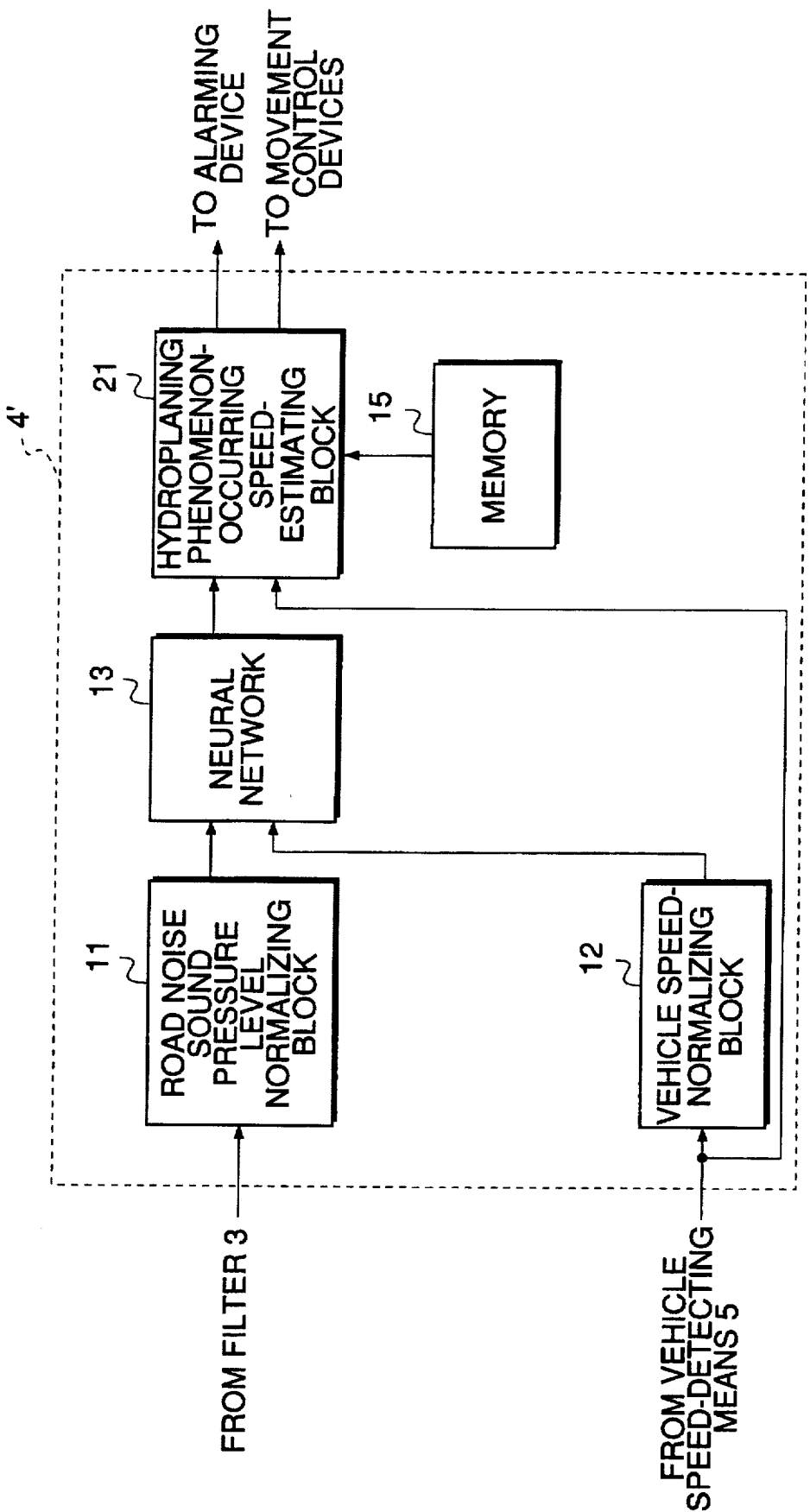

METHOD AND DEVICE FOR ESTIMATING HYDROPLANING-OCCURING VEHICLE SPEED AND METHOD AND DEVICE FOR DETECTING POSSIBILITY OF OCCURENCE OF HYDROPLANING

BACKGROUND OF THE INVENTION

1. Field of the Invention

This invention relates to a method and a device for estimating hydroplaning-occurring vehicle speed, which estimates the speed of a vehicle at and above which a hydroplaning phenomenon of the vehicle can occur, and a method and a device for detecting the possibility of occurrence of the hydroplaning phenomenon.

2. Prior Art

When a vehicle gradually increases its speed during traveling on a wet road surface, a hydroplaning phenomenon can occur that vehicle wheels are lifted up from the road surface due to a water film on the road surface so that the vehicle cannot be controlled by braking. Conventionally, a method of detecting the possibility of occurrence of a hydroplaning phenomenon is known, which detects a change in the rotational speed of the front wheels of a vehicle, and judges if a hydroplaning phenomenon is likely to occur, based on the detected speed change.

Further conventionally, devices for detecting a road surface condition have been also proposed, which detect the condition of the road surface on which a vehicle is traveling, based on road noise generated by wheels of the vehicle. The assignee of this application has also proposed road surface condition-detecting devices by Japanese Laid-Open Patent Publication (Kokai) No. 6-50878 and Japanese Laid-Open Patent Publication (Kokai) No. 7-156782. The device disclosed in Japanese Laid-Open Patent Publication (Kokai) No. 6-50878 first detects road noise generated by wheels of a vehicle, compares a sound pressure signal indicative of the detected road noise with sound pressure data stored in sound pressure data storage means, and determines a surface condition of the road, based on the comparison results as well as vehicle speed detected by vehicle speed-detecting means and ambient temperature detected by ambient temperature-detecting means, to thereby accurately determine the road surface condition on a real time basis. The device disclosed in Japanese Laid-Open Patent Publication (Kokai) No. 7-156782 detects road noise generated by wheels of a vehicle and determines a road surface condition based on a pattern formed by respective levels of frequency components of the detected road noise by the use of a neural network.

The above-mentioned conventional method of detecting the possibility of occurrence of a hydroplaning phenomenon can detect the possibility of occurrence of a hydroplaning phenomenon insofar as the method is applied to vehicles of a rear-wheel drive type. However, since the method determines the possibility of occurrence of a hydroplaning phenomenon from the rotational speed of the front wheels, it cannot be applied to vehicles of a front-wheel drive type, in which a driving force is given to the front wheels. That is, if a change in the rotational speed of the front wheels occurs due to a sharp change in the driving force or an undulation of the road surface, for example, it is erroneously detected that a hydroplaning phenomenon can occur.

On the other hand, although the above-mentioned road surface condition-detecting devices can accurately determine the road surface condition, it has not been undertaken to apply the devices to detecting the possibility of occurrence of a hydroplaning phenomenon based on the detected road surface condition.

SUMMARY OF THE INVENTION

It is a first object of the invention to provide a method and a device for estimating hydroplaning-occurring vehicle speed, which is capable of accurately estimating the speed of a vehicle at and above which a hydroplaning phenomenon can occur, irrespective of the wheel drive type of the vehicle.

It is a second object of the invention to provide a method and a device for detecting the possibility of occurrence of a hydroplaning phenomenon, which is capable of accurately detecting the possibility of occurrence of a hydroplaning phenomenon, irrespective of the wheel drive type of the vehicle.

To attain the first object, the present invention provides a method of estimating a hydroplaning-occurring speed of a vehicle, comprising the steps of:

(1) detecting an amount of water on a wet road surface on which the vehicle is traveling; and (2) estimating a speed of the vehicle at and above which a hydroplaning phenomenon can occur, based on the detected amount of water.

Preferably, the above step (1) comprises detecting road noise generated by at least one of the wheels of the vehicle during traveling of the vehicle, and detecting the amount of water on the wet road surface, base on the detected road noise.

Also preferably, the road noise is detected by means of a neural network.

To attain the second object, the present invention provides a method of detecting a possibility of occurrence of a hydroplaning phenomenon of a vehicle, comprising the steps of:

(1) detecting an amount of water on a wet road surface on which the vehicle is traveling;

(2) detecting a speed of the vehicle; and (3) determining whether there is a possibility that a hydroplaning phenomenon can occur, based on the detected amount of water and the detected speed of the vehicle.

Preferably, the above step (1) comprises detecting road noise generated by at least one of the wheels of the vehicle during traveling of the vehicle, and detecting the amount of water on the wet road surface, base on the detected road noise.

To attain the first object, the present invention provides a device for estimating a hydroplaning-occurring speed of a vehicle having wheels, comprising:

road noise-detecting means arranged in the vicinity of at least one of the wheels of the vehicle for detecting road noise generated by the at least one of the wheels;

means for extracting data of a parameter indicative of frequency components of the road noise, from the road noise detected by the road noise-detecting means;

water amount-detecting means for detecting an amount of water on a road surface on which the vehicle is traveling, based on the data of the parameter indicative of the frequency components of the road noise, by means of a neural network; and vehicle speed-estimating means for estimating a speed of the vehicle at and above which a hydroplaning phenomenon of the vehicle can occur, based on the detected amount of water.

To attain the second object, the present invention provides a device for detecting a possibility of occurrence of a hydroplaning phenomenon of a vehicle having wheels, comprising:

road noise-detecting means arranged in the vicinity of at least one of the wheels of the vehicle for detecting road noise generated by the at least one of the wheels;

means for extracting data of a parameter indicative of frequency components of the road noise, from the road noise detected by the road noise-detecting means;

water amount-detecting means for detecting an amount of water on a road surface on which the vehicle is traveling, based on the data of the parameter indicative of the frequency components of the road noise, by means of a neural network; and hydroplaning-determining means for determining a possibility of occurrence of the hydroplaning phenomenon of the vehicle, based on the detected amount of water and the detected speed of the vehicle.

The above and other objects, features, and advantages of the invention will become more apparent from the following detailed description taken in conjunction with the accompanying drawings.

BRIEF DESCRIPTION OF THE DRAWINGS

FIG. 7 is a view showing an example of a map prepared based on the relationship in FIG. 6; and FIG. 8 is a block diagram showing details of the construction of a control block of a device for estimating hydroplaning-occurring vehicle speed, which utilizes the method of estimating hydroplaning-occurring vehicle speed according to the present invention.

DETAILED DESCRIPTION

The invention will be described in detail with reference to drawings showing embodiments thereof.

Figure 1:
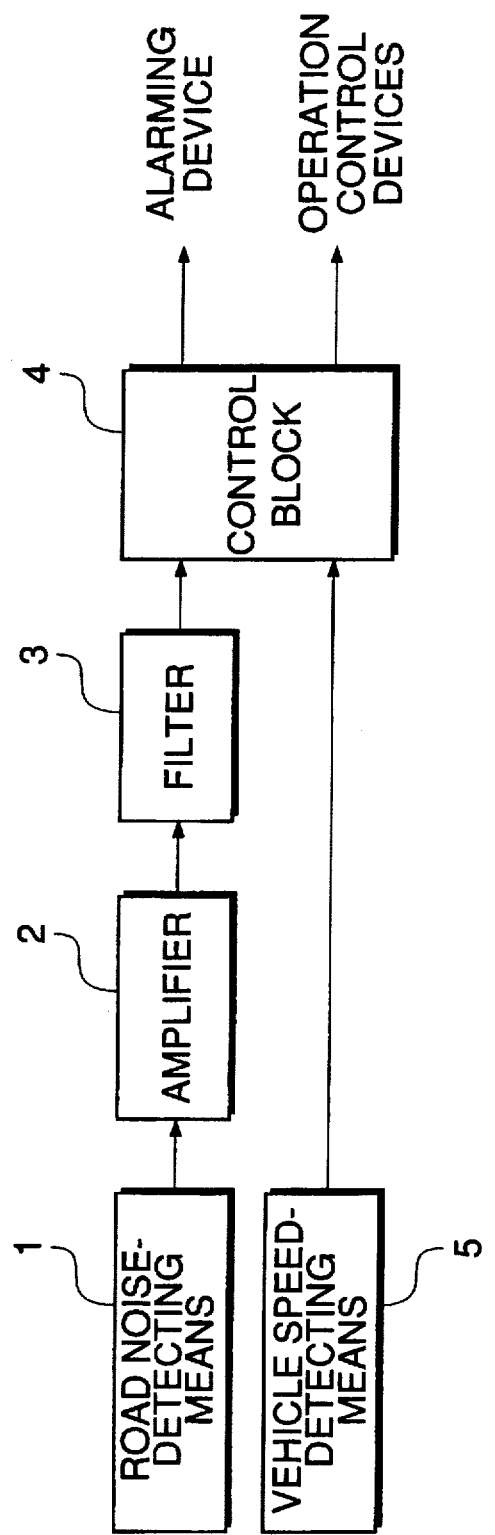
FIG. 1 is a schematic block diagram showing the arrangement of a device for detecting the possibility of occurrence of a hydroplaning phenomenon, to which is applied the method of detecting the possibility of a hydroplaning phenomenon according to a first embodiment of the invention.

Referring first to FIG. 1, there is shown the arrangement of a device for detecting the possibility of occurrence of a hydroplaning phenomenon to which is applied the method of detecting the possibility of occurrence of a hydroplaning phenomenon according to a first embodiment of the invention.

In the figure, reference numeral 1 designates road noise-detecting means for detecting road noise generated by wheels of a vehicle, which is implemented in the present embodiment by a microphone. The road noise-detecting means 1 has an output thereof connected to one input of a control block 4, via an amplifier 2 for amplifying the road noise and a filter 3 for filtering out a selected frequency component out of the amplified road noise. The control block 4 detects a road surface condition in which the vehicle in which the present device is installed is traveling, particularly an amount of water on a wet road surface by the use of a neural network and determines whether there is any probability or possibility of occurrence of a hydroplaning phenomenon, based on the detected road surface condition. Connected to the other input of the control block 4 is an output of vehicle speed-detecting means 5 for detecting the speed of the vehicle. Based on the determination results, the control block 4 controls operations of various movement control devices and systems such as an alarming device, an anti-lock brake system, a power steering system, and a four wheel drive system, none of which is shown.

Figure 2:
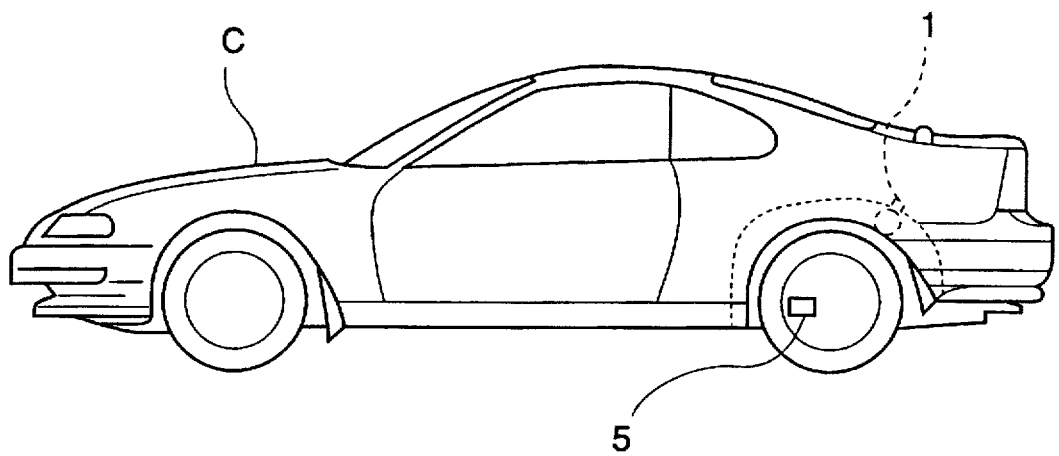
FIG. 2 is a schematic view showing the locations of a road noise sensor and a vehicle speed sensor, both appearing in FIG. 1, mounted in a vehicle.

FIG. 2 shows the locations of the road noise-detecting means 1 and the vehicle speed-detecting means 5 in the vehicle.

In the figure, symbol C designates the vehicle which is a front-engine type, and the microphone as the road noise-detecting means 1 is arranged in the interior of at least one of wheel houses of left and right rear wheels of the vehicle at such locations as are less affected by noise generated by the engine, and in such a fashion that it is not directly hit by gravels or splashed water. The vehicle speed-detecting means 5 is arranged in the interior of at least one of the left and right rear wheels at a predetermined location. The vehicle speed-detecting means 5 generates an electric pulse signal corresponding to the wheel speed.

A road surface condition-detecting method which is one of control processings carried out by the control block 4 will be explained hereinafter with reference to FIGS. 3 to 5.

Figure 3:
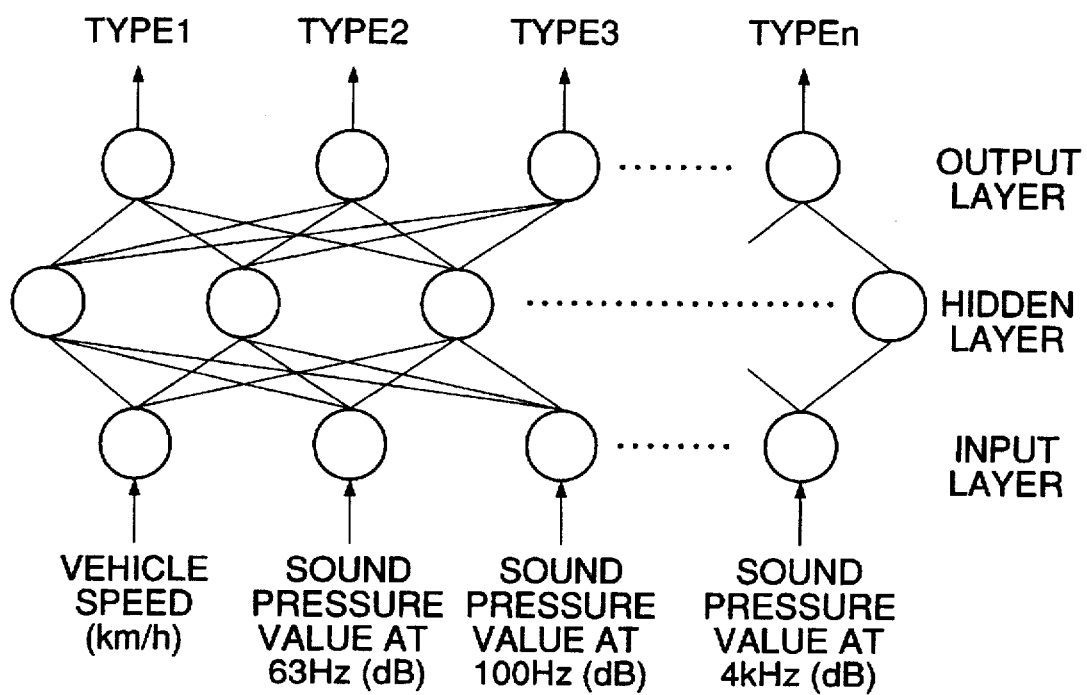
FIG. 3 is a schematic view showing a neural network used in the first embodiment.
Figure 4:
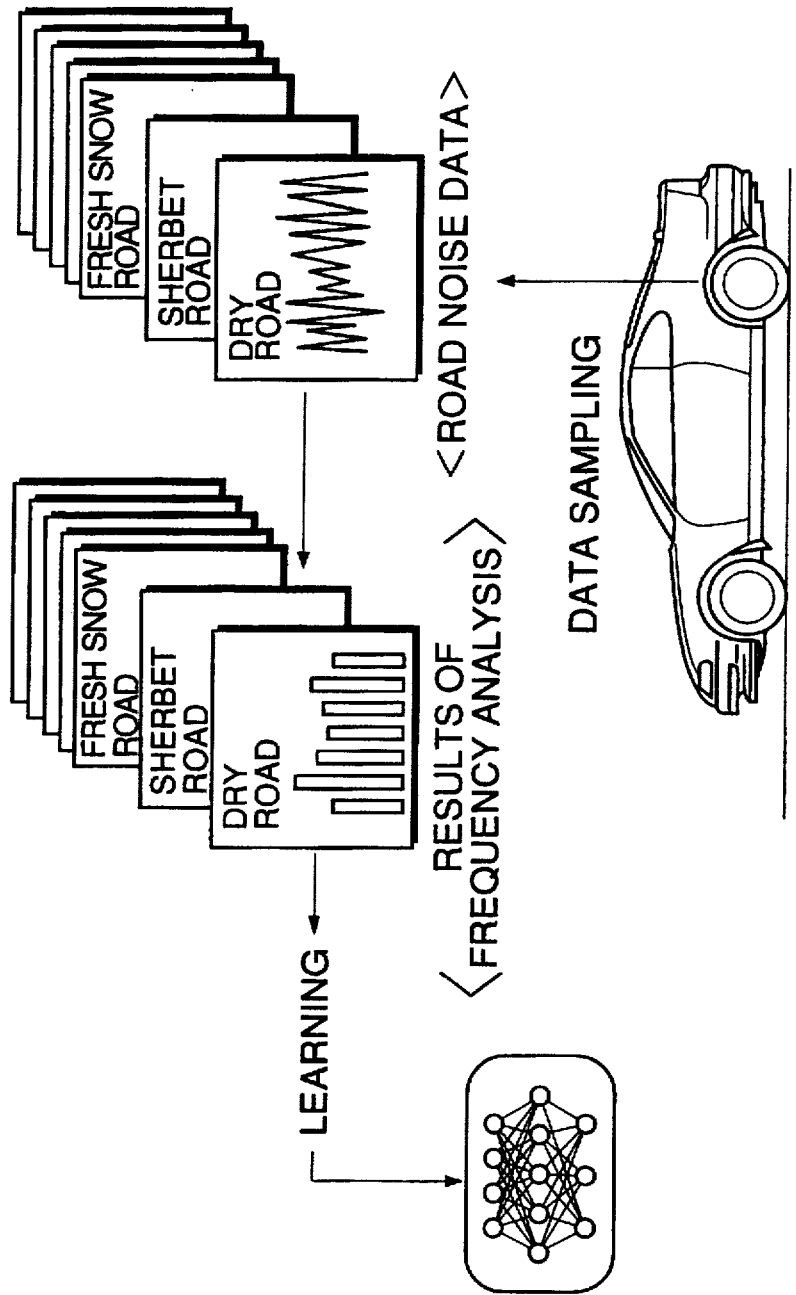
FIG. 4 is a view useful in explaining a manner in which learning is carried out by the neural network model in FIG. 3.

FIG. 3 shows an example of a neural network which is used in the present embodiment. The neural network model employed in the present embodiment has a three-layer structure formed of an input layer, an intermediate or hidden layer, and an output layer, and uses a learning algorithm called "Back Propagation" (hereinafter referred to as "BP"), details of which are disclosed in Japanese Laid-open Patent Publication (Kokai) No. 7-156782.

As shown in FIG. 3, in the present embodiment, pieces of information are input to units or nodes of the input layer, which are indicative of the vehicle speed and sound pressure levels of respective particular frequencies detected over respective one-third octave bands. These pieces of information are weighted by weights constituting a connection matrix between the input layer and the hidden layer and input to the units or nodes of the hidden layer. In the hidden layer, an output from each of the units is determined by a sigmoidal function, for example. Similarly to the data processing carried out when data are transferred from the input layer to the hidden layer, outputs from the units of the hidden layer are weighted by weights constituting a connection matrix between the hidden layer and the output layer, and the weighted outputs are input to units of the output layer. Further, in the output layer, similarly to the processing carried out in the hidden layer, the outputs from the units or nodes are determined by the sigmoidal function.

The output from each unit or node of the output layer is a value of the sigmoidal function, which falls between 0 to 1. That is, each unit from the output layer delivers a value indicative of "probability". By the values of "probability" delivered from the units or nodes of the output layer, one of types TYPEn corresponding to an actual road surface condition is determined. In the present embodiment, an amount of water on a wet road surface is detected as the road surface condition, and therefore each of the types TYPEn indicates the amount of water on the road on which the vehicle is traveling.

The learning by the use of the BP learning algorithm described above is intended to make agreement between output values delivered from the third layer (output layer) when input values are applied to the first layer (input layer) and the probabilities of respective desired types TYPEn of the condition of the road surface on which the vehicle is actually traveling. More specifically, as shown in FIG. 4, road noise from the wheel(s) is detected by the road noise-detecting means 1, and the detected road noise is sampled. The sampled data is subjected to frequency analysis to obtain data of sound pressure levels of respective particular frequency components. The data of sound pressure levels are input to the input layer together with the vehicle speed data as described above with reference to FIG. 3. Then, the weights of the connection matrix are determined such that the actual road surface condition agrees with each of the types of the road surface condition indicated by final outputs (probabilities) from the output layer.

Figure 5:
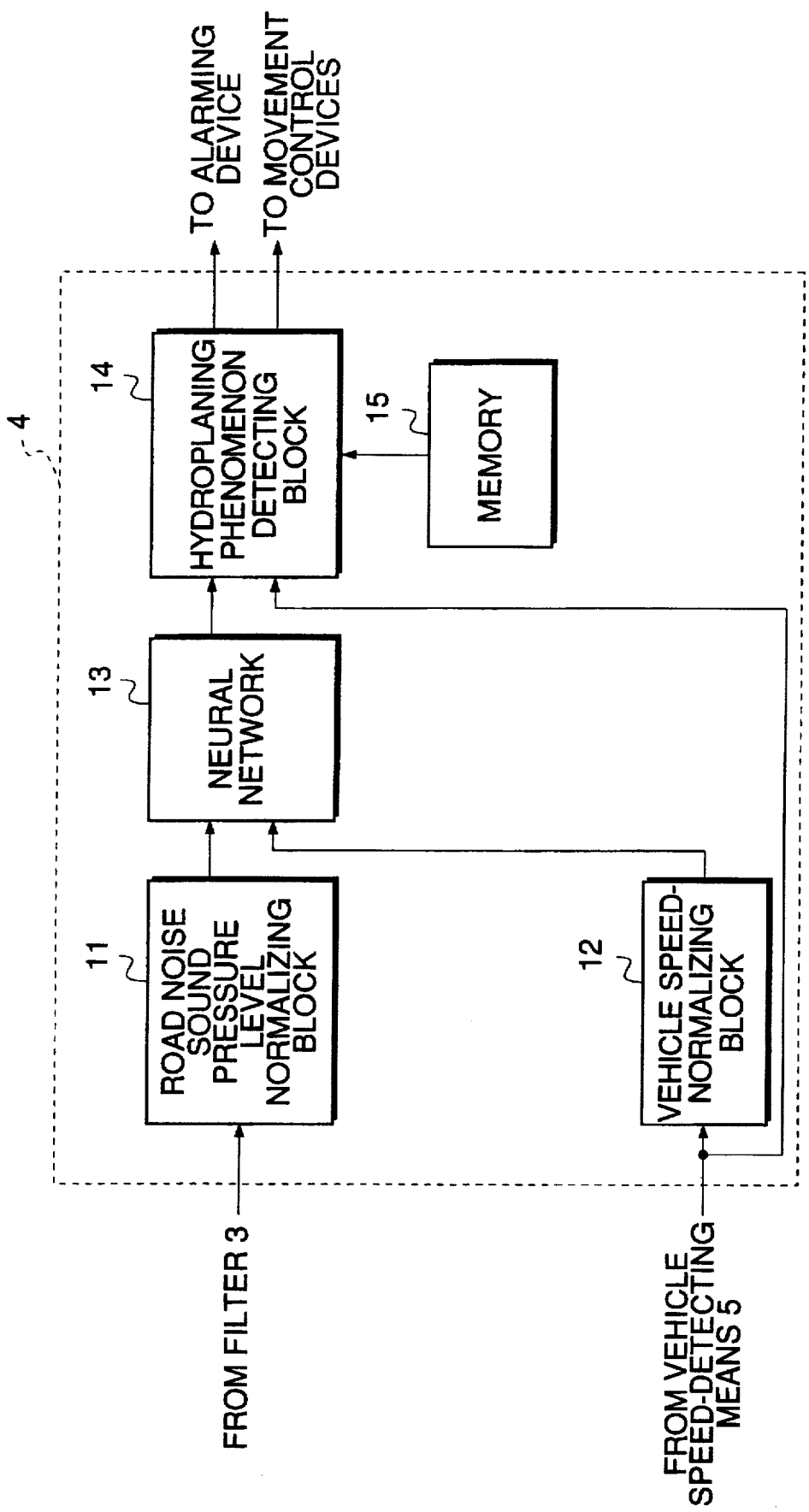
FIG. 5 is a block diagram showing details of the construction of a control block in FIG. 1.

FIG. 5 shows details of the construction of the control block 4 in FIG. 1.

As shown in FIG. 5, the control block 4 includes a pressure sound level-normalizing block 11 which normalizes the sound pressure level of each particular frequency band (in this embodiment, each one-third octave band) of road noise which is obtained by the frequency analysis carried out by the filter 3 to a value falling within a range from 0 to 1, a vehicle speed-normalizing block 12 which normalizes a vehicle speed value obtained by the vehicle speed-detecting means 5 to a value falling within the range from 0 to 1, a neural network 13 which receives outputs from the vehicle speed-normalizing block 12 and the sound pressure level-normalizing block 11 and detects a road surface condition based on the results of learning, and a hydroplaning-detecting block 14 which detects a probability of occurrence of a hydroplaning phenomenon, based on the amount of water on a wet road surface detected by the neural network 13, the vehicle speed detected by the vehicle speed-detecting means 5, and a hydroplaning phenomenon-detecting map stored in a memory 15 which will be described later. The hydroplaning phenomenon-detecting block 14 outputs control signals to various movement control and devices systems including the alarming device according to the detected probability of occurrence of hydroplaning phenomenon.

Figure 6:
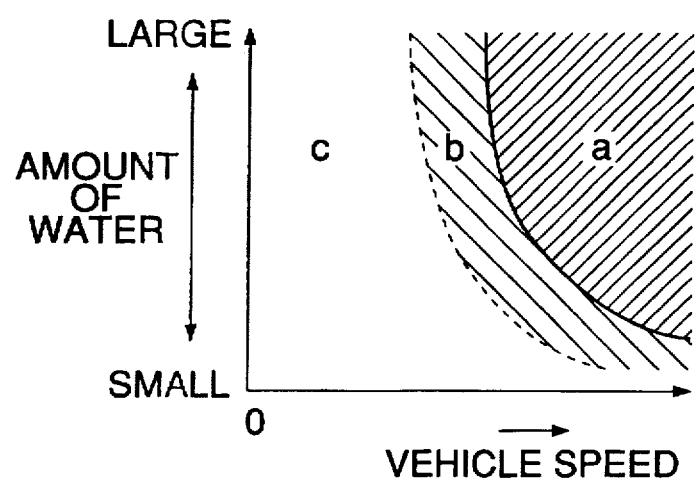
FIG. 6 is a graph showing the relationship between the traveling speed of a vehicle, an amount of water on a wet road surface on which the vehicle is traveling, and a vehicle speed-water amount region in which a hydroplaning phenomenon can occur.

FIG. 6 shows the relationship between the traveling speed of a vehicle, an amount of water on a wet road surface on which the vehicle is traveling, and a vehicle speed-water amount region in which a hydroplaning phenomenon can occur. In the figure, the vehicle speed is taken on the abscissa and the amount of water is taken on the ordinate. As shown in FIG. 6, a region "a" represents a hydroplaning phenomenon-alarming region in which there is a high probability that a hydroplaning phenomenon will occur, a region "b" a hydroplaning phenomenon-watching region in which there is a likelihood that a hydroplaning phenomenon will occur, and a region "c" an OK region in which there is almost no probability that a hydroplaning phenomenon will occur.

FIG. 7 shows a map prepared based on the relationship of FIG. 6, which is stored in the memory 15 shown in FIG. 5. As shown in FIG. 7, according to this map, there are provided six predetermined values of an amount of water on a wet road surface, and predetermined values of the vehicle speed which differ from each other by an interval of 10 km/h. Each lattice point in the map is given a numerical value "2", "1" or "0" depending on which of the regions "a" "b" and "c" shown in FIG. 6 the region determined by the water amount and the vehicle speed belongs to. Needless to say, the manner of dividing the amount of water and the vehicle speed is not limited to the one shown in FIG. 7.

The control operation carried out by the device for detecting the possibility of occurrence of a hydroplaning phenomenon having the above construction will now be explained.

When the vehicle is traveling on a road surface, the road noise-detecting means 1 detects road noise generated by wheels of the vehicle. The amplifier 2 and the filter 3 analyze the frequency of the detected road noise. The sound pressure level normalizing block 11 normalizes the sound pressure value of the frequency-analyzed road noise. The vehicle speed-normalizing block 12 normalizes the vehicle speed value detected by the vehicle speed-detecting means 5. The normalized vehicle speed value and the normalized road noise value are fed to the units or nodes of the input layer of the neural network 13.

Based on results obtained by the aforementioned learning, the neural network 13 detects the road surface condition, particularly, the amount of water on a wet road surface. Based on the detected amount of water and the detected vehicle speed, the hydroplaning phenomenon-detecting block 14 retrieves the map stored in the memory 15 and reads out a corresponding value, namely, one of the three values "2","1" or "0" and delivers a control signal based on the read-out value to the alarming device.

In this embodiment, the alarming device is comprised of an alarming lamp which selectively emits light in "green", "yellow" or "red", and an alarming buzzer which selectively generates beep sound or long beep sound.

If the value "0" is read out from the memory 15, which means that there is almost no probability of occurrence of a hydroplaning phenomenon, the hydroplaning phenomenon-detecting block 14 outputs the control signal to make the alarming lamp emit light in "green" and inhibit the operation of the buzzer. If the value "1" is read out from the memory 15, which means that the probability of occurrence of a hydroplaning phenomenon is increased, the hydroplaning phenomenon-detecting block 14 outputs the control signal to make the alarming lamp emit light in "yellow" and make the buzzer generate beep sound. If the value "2" is read out from the memory 15, which means that a hydroplaning phenomenon will surely occur, the hydroplaning phenomenon-detecting block 14 outputs the control signal to make the alarming lamp emit light in "red" and make the buzzer generate long beep sound.

When the hydroplaning phenomenon-detecting block 14 detects the probability or possibility of occurrence of a hydroplaning phenomenon, it may output a control signal which electrically causes a throttle valve of the engine to a related one of the above mentioned movement control devices in addition to the above-mentioned alarming control signal.

As described above, according to the present embodiment, a water amount-vehicle speed region in which a hydroplaning phenomenon will occur can be accurately detected by detecting the amount of water on a wet road surface, irrespective of the wheel drive type of the vehicle.

An embodiment of the device for estimating a hydroplaning-occurring vehicle speed to which the method for estimating a hydroplaning-occurring vehicle speed according to the present invention will be explained hereinafter.

In the previous embodiment, the water amount-vehicle speed region in which a hydroplaning phenomenon will occur is detected based on the amount of water on the road surface detected by means of the neural network and the vehicle speed detected by the vehicle speed-detecting means. The present embodiment differs from the previous embodiment only in that a vehicle speed at and above which there is a high probability of occurrence of a hydroplaning phenomenon is estimated based on an amount of water detected by a neural network using a map similar to the map used in the previous embodiment. Therefore, this embodiment has a construction similar to the construction of the previous embodiment shown in FIGS. 1, 3, and 4. Elements and parts corresponding to those of the previous embodiment are designated by identical reference numerals and description thereof is omitted.

FIG. 8 shows the construction of a control block 4' which corresponds to the control block shown in FIG. 5 of the previous embodiment. As shown in FIG. 8, the present embodiment is provided with a hydroplaning phenomenon-occurring vehicle speed-estimating block 21 in place of the hydroplaning phenomenon-detecting block 14 in FIG. 5.

The control operation carried out by the present embodiment will be described hereinbelow.

When the vehicle is traveling on a road surface, the road noise-detecting means 1 detects road noise generated by wheels of the vehicle. The amplifier 2 and the filter 3 analyze the frequency of the detected road noise. The sound pressure-normalizing block 11 normalizes the sound pressure value of the road noise having been subjected to the frequency analysis. At the same time, the vehicle speed-normalizing block 12 normalizes the vehicle speed value detected by the vehicle speed-detecting block 5. The normalized vehicle speed value and the normalized road noise value are fed to the units of the input layer of the neural network 13. The neural network 13 detects the road surface condition, particularly, the amount of water on a wet road surface based on the learning results similarly to the previous embodiment. Based on the detected amount of water, the hydroplaning phenomenon-occurring speed-estimating block 21 retrieves the map stored in the memory 15 and detects a vehicle speed range in which the value "2" is read out first and determines an upper limit value of the detected vehicle speed range as an estimated value of the vehicle speed at and above which a hydroplaning phenomenon will occur.

The hydroplaning phenomenon-occurring vehicle speed-estimating block 21 informs the driver of the estimated vehicle speed value by any desired means such as a display device which is not shown and warns the driver by comparing the estimated vehicle speed value with the detected actual vehicle speed value.

In the case that the vehicle on which the present device is installed is provided with an automatic cruising function, it may be so programmed that an automatic cruising speed which exceeds the estimated vehicle speed value cannot be set.

As described above, according to the present embodiment, the vehicle speed at and above which there is a high probability of occurrence of a hydroplaning phenomenon can be accurately estimated by detecting the amount of water on the road surface, irrespective of the wheel drive type of the vehicle.

Although in the above described embodiments the neural network is used for determining the road surface condition, this is not limitative, but other road surface condition-determining means may be used to detect the amount of water on a wet road surface. Further, although in the above described embodiments the amount of water on a wet road surface is estimated from road noise, as a preferable method, any other method may be employed to detect the amount of water on a wet road surface.

As has been described heretofore, according to the invention, to estimate hydroplaning-occurring vehicle speed, the amount of water on the road surface on which the vehicle is traveling is detected, and based on the detected amount of water, the vehicle speed at and above which a hydroplaning phenomenon can occur is estimated. As a result, the vehicle speed at and above which there is a high probability of occurrence of a hydroplaning phenomenon can be accurately detected, irrespective of the wheel drive type of the vehicle.

Furthermore, according to the invention, to detect the possibility of occurrence of a hydroplaning phenomenon, the amount of water on the road surface on which the vehicle is traveling and the vehicle speed are detected, and based on the detected amount of water and the detected vehicle speed, the possibility of occurrence of a hydroplaning phenomenon is detected. As a result, the possibility of occurrence of a hydroplaning phenomenon can be accurately detected, irrespective of the wheel drive type of the vehicle.

While the invention has been described in detail and with reference to specific embodiments thereof, it will be apparent to those skilled in the art that various changes and modifications may be made therein without departing from the spirit and scope of the invention.

What is claimed is:

1. A method of estimating a hydroplaning-occurring speed of a vehicle, comprising the steps of:
   (1) detecting an amount of water on a wet road surface on which said vehicle is traveling; and
   (2) estimating a speed of said vehicle at and above which a hydroplaning phenomenon can occur, based on the detected amount of water.

2. A method as claimed in claim 1, wherein said vehicle has wheels, said step (1) comprising detecting road noise generated by at least one of said wheels of said vehicle during traveling of said vehicle, and detecting said amount of water on said wet road surface, base on the detected road noise.

3. A method as claimed in claim 1, wherein said road noise analyzed using a neural network.

4. A method of detecting a possibility of occurrence of a hydroplaning phenomenon of a vehicle, comprising the steps of:
   (1) detecting an amount of water on a wet road surface on which said vehicle is traveling;
   (2) detecting a speed of said vehicle; and
   (3) determining whether there is a possibility that a hydroplaning phenomenon can occur, based on the detected amount of water and the detected speed of said vehicle.

5. A method as claimed in claim 4, wherein said vehicle has wheels, said step (1) comprising detecting road noise generated by at least one of said wheels of said vehicle during traveling of said vehicle, and detecting said amount of water on said wet road surface, base on the detected road noise.

6. A device for estimating a hydroplaning-occurring speed of a vehicle having wheels, comprising:
   road noise-detecting means arranged in the vicinity of at least one of said wheels of said vehicle for detecting road noise generated by said at least one of said wheels;

means for extracting data of a parameter indicative of frequency components of said road noise, from said road noise detected by said road noise-detecting means;

water amount-detecting means for detecting an amount of water on a road surface on which said vehicle is traveling, based on said data of said parameter indicative of said frequency components of said road noise, by means of a neural network; and vehicle speed-estimating means for estimating a speed of said vehicle at and above which a hydroplaning phenomenon of said vehicle can occur, based on the detected amount of water.

7. A device for detecting a possibility of occurrence of a hydroplaning phenomenon of a vehicle having wheels, comprising:

road noise-detecting means arranged in the vicinity of at least one of said wheels of said vehicle for detecting road noise generated by said at least one of said wheels;

means for extracting data of a parameter indicative of frequency components of said road noise, from said road noise detected by said road noise-detecting means;

water amount-detecting means for detecting an amount of water on a road surface on which said vehicle is traveling, based on said data of said parameter indicative of said frequency components of said road noise, by means of a neural network; and hydroplaning-determining means for determining a possibility of occurrence of said hydroplaning phenomenon of said vehicle, based on the detected amount of water and the detected speed of said vehicle.

* * * * *